US006746675B2

United States Patent
Goino

(10) Patent No.: US 6,746,675 B2
(45) Date of Patent: Jun. 8, 2004

(54) PHYSIOLOGICALLY ACTIVE COMPOSITIONS BASED UPON ACTIVE INGREDIENTS OF BASIDIOMYCOTINA AND ARALIACEAE

(75) Inventor: Tadashi Goino, 7362-1, Ariake, Hodaka-cho, Minamiazumi-gun (JP)

(73) Assignee: Tadashi Goino, Nagano (JP)

( * ) Notice: Subject to any disclaimer, the term of this patent is extended or adjusted under 35 U.S.C. 154(b) by 0 days.

(21) Appl. No.: 10/182,426
(22) PCT Filed: Jan. 31, 2001
(86) PCT No.: PCT/JP01/00650
§ 371 (c)(1), (2), (4) Date: Oct. 21, 2002
(87) PCT Pub. No.: WO01/56589
PCT Pub. Date: Aug. 9, 2001

(65) Prior Publication Data
US 2003/0104005 A1 Jun. 5, 2003

(30) Foreign Application Priority Data
Jan. 31, 2000 (JP) ......................... 2000-022724

(51) Int. Cl.$^7$ ......................... A61K 35/78; A61K 35/84; A61P 3/10
(52) U.S. Cl. ................... 424/195.15; 424/725; 424/728
(58) Field of Search ........................... 424/195.15, 725, 424/728

(56) References Cited

PUBLICATIONS

Wang et al. "Alteration of pulse in human subjects by three Chinese herbs", Biosciences Information Service, Philadelphia, Pa., see entire article especially the abstract (1994).*
Yun Taik–Koo, Updated from Asia: Asian studies on cancer chemoprevention, Biosciences Information Service, Philadelphia, PA, Abstract (1999).
O.A. Bocharova et al, "Testing plant–based drugs for prevention and nontoxic theraphy of cancer diseases on experimental models,", Biosciences Information Service, Philadelphia, PA, Abstract, and Vestnik Rossiiskoi Akademii Meditsinskikh Nauk, No. 2, p. 52–55, (1994).
Zee–Cheng et al, "Ten Significant Tonic Decoction, SQT: A potent Chinese biological response modifier in cancer immunotheraphy, potentiation and detoxificatin of anticancer drugs.", Biosciences Information Service, Philadelphia, P., Abstract (1992).
Wang Wei Kung et al, "Alteration of pulse in human subjects by three Chinese herbs", Biosciences Information Service, Philadelphia, PA, Abstract (1994).
Oh William K et al, "Activity of the herbal combination, PC–SPES, in the treatment of patients with androgen–independent prostate cancer", Biosciences Information Service, Philadelphia, PA, abstract (2001).

* cited by examiner

Primary Examiner—Christopher R. Tate
Assistant Examiner—Randall O. Winston
(74) Attorney, Agent, or Firm—Conley Rose, P.C.

(57) ABSTRACT

Compositions are taught that may comprise active components of one or more types of Basidiomycotina that belong to polyporaceae Basidiomycotina and active components of the root of a plant that belongs to Araliaceae. Such compositions have shown hypoglycemic effects and anti-tumor activity. More preferably, the Basidiomycotina may be *Ganoderma Lucidum* and/or *Coriolus versicolor* and the plant that belongs to Araliaceae may be medicinal ginseng, e.g. *Panax ginseng* and/or *Panax japonicus*. Preferably, an aqueous solution of the composition has an oxidation-reduction potential of less than about 1230 mV, more preferably less than about 900 mV and most preferably less than about 330 mV. Methods for making such compositions are also taught and may include hot water extraction of the above-mentioned components. Furthermore, methods for treating patients are also taught and include administering a therapeutically effective amount of one or more of the present compositions.

44 Claims, No Drawings

PHYSIOLOGICALLY ACTIVE COMPOSITIONS BASED UPON ACTIVE INGREDIENTS OF BASIDIOMYCOTINA AND ARALIACEAE

This application claims priority from PCT Application PCT/JP01/00650 filed Jan. 31, 2001 which claims priority from Japanese Patent Application 2000-22724 filed Jan. 31, 2000.

TECHNOLOGICAL FIELD

The present invention concerns compositions having physiological activities, including but not limited to anti-tumor activity and hypoglycemic effects (i.e. blood sugar level reducing effects). More particularly, compositions are taught that comprise active ingredients found in extracts of the fruiting bodies and/or mycelia culture (including the culture solution in addition to the mycelia) of fungi that belong to polyporaceae Basidiomycotina, such as *Ganoderma Lucidum* and/or *Coriolus versicolor*, and extracts obtained from the root of a Araliaceae plant. Methods for making and using such compositions are also taught.

DESCRIPTION OF THE RELATED ART

The fruiting bodies and mycelium culture (which means only the mycelium and the mixture of the mycelium and the culture solution of the mycelium, hereinafter simply referred to as "the culture") of *Ganoderma Lucidum*, which belongs to aphyllophoral polyporaceae Basidiomycotina, have been known as natural medicines since ancient times. In addition to its various beneficial effects, it has been known that the polysaccharides and other low molecular weight components contained in these medicines have a variety of anti-tumor activities. Also, substances having various physiological activities, including anti-tumor activities, also have been extracted from the fruiting bodies of *Coriolus versicolor*, which belongs to polyporaceae Basidiomycotina.

Moreover, the roots of plants that belong to Araliaceae, including ginseng (*Daucus carota*), and their extracted components, also have independently been used as natural medicines since ancient times, and have been known to have numerous beneficial effects.

SUMMARY OF THE INVENTION

Generally speaking, although various therapeutic methods that incorporate treatment and prophylaxis by means of natural medicines are advantageous, because the natural medicines usually do not have adverse unwanted effects, the efficacy of known natural medicines is often minimal. While it has been empirically and experimentally known that both the extracted components of Basidiomycotina and the extracted components of ginseng have useful beneficial effects, combination of these specific components and the consequent synergistic amplification of their physiological activities caused by combining these components have not been known.

The inventors have discovered that compositions comprising extracted components derived from Basidiomycotina and extracted components derived from the roots of plants that belong to Araliaceae have remarkably potent anti-tumor activity. In addition, the inventors have discovered that such compositions can reduce blood sugar levels in hyperglycemic individuals (hereinafter "hypoglycemic effects"). Although not wishing to be bound by theory, the inventors believe that the physiological activities of these compositions may be related to their oxidation-reduction potential.

Thus, in one aspect of the present teachings, compositions are taught that include active ingredients that are found in one or more types of Basidiomycotina that belong to polyporaceae Basidiomycotina and active ingredients that are found in the root of a plant that belongs to Araliaceae. The active ingredients may be synthetically made or may be extracted, for example, from *Ganoderma Lucidum* and/or *Coriolus versicolor* and medicinal ginseng, which may be, e.g., *Panax ginseng* and/or *Panax japonicus*. The compositions preferably exhibit an oxidation-reduction potential of less than about +1230 mV, when dissolved in an aqueous solution, and more preferably less than about +900 mV. Such compositions may comprise a therapeutically effective amount of the active ingredients of these components. Such compositions may be administered, for example, to patients having tumors and/or to patients having high blood glucose levels.

Although the present teachings specifically contemplate active ingredients extracted from natural products, of course, synthetically made active ingredients that exhibit the herein-described effects are also contemplated.

In another aspect of the present teachings, compositions are taught that include extracted components of one or more types of Basidiomycotina that belong to polyporaceae Basidiomycotina and extracted components of the root of a plant that belongs to Araliaceae. Preferably, the oxidation-reduction potential of such compositions is about +1230 mV or less.

In another aspect of the present teachings, compositions are taught in which *Ganoderma Lucidum* and/or *Coriolus versicolor* is/are the above-mentioned one or more types of Basidiomycotina.

In another aspect of the present teachings, compositions are taught that comprises a therapeutically effective amount of the above-mentioned components. In one representative example, the compositions comprise components extracted from between about 0.5 and 2 parts per weight of the root of an Araliaceae plant and about 2 parts per weight of the above-mentioned Basidiomycotina. Preferably, the components are extracted from the fruiting bodies of Basidiomycotina. The Araliaceae plant preferably belongs to the family of medicinal ginseng and more preferably, the Araliaceae plant is *Panax ginseng* and/or *Panax japonicus*.

In another aspect of the present teachings, compositions are taught that may be utilized as anti-tumor agents. In another aspect of the present teachings, compositions are taught that exhibit hypoglycemic effects. Methods of treatment utilizing such compositions are provided.

Various methods of manufacturing such compositions having such physiological activities are also taught. Representative examples are provided, such as obtaining components from a solution having an appropriate oxidation-reduction potential, which solution can be obtained by hot water extraction of one or more types of polyporaceae Basidiomycotina and the root of an Araliaceae plant. Preferably, the one or more types of Basidiomycotina may be *Ganoderma Lucidum* and/or *Coriolus versicolor*. Such components may be extracted in a ratio of about 0.5 and 2 parts per weight of Araliaceae root to about 2 parts per weight of the above-mentioned Basidiomycotina. The Araliaceae root preferably is medicinal ginseng and more preferably is *Panax ginseng* and/or *Panax japonicus*. Naturally, therapeutically effective compositions may be manufactured using different techniques that provide substantially the same effects.

Other objects, features and advantages of the present invention will be readily understood after reading the following detailed description together with the accompanying claims.

DETAILED DESCRIPTION OF THE INVENTION

The active ingredients of the present compositions may be made in various ways, including but not limited to synthesis techniques or isolation techniques. In one preferred method of making the present compositions, the active ingredients are derived from the extracted components of one or more types of Basidiomycotina that belong to polyporaceae Basidiomycotina and the extracted components of the root of a plant that belongs to Araliaceae. Polyporaceae Basidiomycotina includes *Ganoderma Lucidum, Coriolus versicolor* and other related fungi. More preferably, the extracted components can be obtained from the fruiting bodies and/or mycelium culture (including the culture solution in addition to the mycelia) of one or more types of Polyporaceae.

Preferably, the Basidiomycotina is selected from one or more types of *Ganoderma Lucidum* and *Coriolus versicolor*. More preferably, a combination of *Ganoderma Lucidum* and *Coriolus versicolor* may be used. Taxonomical identification of the types of Basidiomycotina used herein is based on identifications provided in "Primary Color Picture Book of Japanese Mushrooms" written by Imazeki and Hongou (Hoiku Co).

One representative example of *Ganoderma Lucidum* is Reishi fungus (*Ganoderma Lucidum*). Although this fungus breeds well on trees in nature, the native fungus is scarce. However, it can also be artificially cultivated. The fungus is glossy and consists of a waxy cap and a stalk having a length that may reach approximately 15 cm. The color of the fruiting body is red, blue, yellow, white, purple and black. The fungus has white strands and grows on tree stumps and/or around the base of a tree weakened by a disease.

*Coriolus versicolor* fungus naturally grows in the western part of Japan, especially in Shinshuu (particularly in Nagano Prefecture) and the Shikoku and Kyushu islands. In nature, this fungus is a xylophilic fungus that breeds especially well on broad-leafed trees. This Basidiomycotina breeds well in nature, can be artificially cultivated and also grown in a cell culture, with no restrictions. Preferably, the naturally grown fungus is used.

Preferably, the fruiting bodies of the fungi and/or a culture of the fungus body are used. The fruiting bodies can be prepared by air-drying at room temperature in the dark.

When *Ganoderma Lucidum* is used, it is particularly recommended to use naturally ripened black fruiting bodies. When *Coriolus versicolor* is used, it is recommended to use naturally grown fruiting bodies that were gathered in summer and air-dried at room temperature in the dark.

Preferably, the medicinal ginseng is an Araliaceae plant, which includes *Panax quinquefolium* L., *Panax notogingseng, Panax japonicus* C. A. Meyer, in addition to *Panax ginseng* C. A. Meyer. Preferably, *Panax ginseng* and/or *Panax japonicus* are used. More preferably, *Panax japonicus* is used. The roots of any of these types of ginseng may be used. Further, a single type of Araliaceae plant can be used or a combination of 2 or more types also can be used. Plants belonging to the Umbelliferae family also can be used as a substitute for the Araliaceae plant.

Suitable compositions can be obtained by extraction techniques using water. Although the extraction can be conducted using water at room temperature, preferably hot water is used. The raw materials for the Basidiomycotina extracted components and the Araliaceae extracted components can be separately extracted using hot water and then these extracts can be mixed, or a mixture of the Basidiomycotina and the root of the Araliaceae plant can be mixed together and extracted using hot water. For extraction using hot water, the raw materials may be crushed, sliced or powdered. Preferably, the raw materials are crushed into splinters. More preferably, splinters are approximately 5 mm in size.

The temperature of the hot water used for the hot water extraction preferably may be between about 80° C. and about 100° C. and more preferably, between about 90° C. and about 95° C. The recommended extraction time is at least 1 hour, preferably 2 hours or more and most preferably 2.5 hours or more. Preferably, the extraction time is limited to about 3 to 4 hours. The extraction process may be conducted using a reflux condenser.

While no special restrictions are placed on the quantity of water used in relation to the extraction raw materials, preferably a ratio of approximately 500 parts per weight of water to about 10 to 20 parts per weight of raw materials is used for the extraction. The concentration of an extraction solution obtained using such a weight ratio (especially if a reflux condenser is used) is typically a suitable concentration for direct administration without additional processing.

The extraction raw materials can be removed from the extraction solution obtained by filtration or other known methods. If needed, the extraction solution filtrate and supernatant can be condensed and used as a concentrated solution. In addition, by evaporating the water component, a solid (powder-like) extracted component can also be obtained and, if needed, the required dry extracted component can be obtained by drying or other known methods.

With respect to the administration form and the dosage form of the composition, additives for pharmaceutical manufacturing or for stabilization of the extracted component naturally can be added during the condensation or drying process.

The extraction raw materials can be used in a ratio of about 15 parts per weight of Basidiomycotina to about 1.5–6 parts per weight of the root of an Araliaceae plant. Preferably, about 2–4 parts per weight of the Araliaceae root is used for about 15 parts per weight of Basidiomycotina. More preferably, about 3 parts per weight of the Araliaceae root is used for about 15 parts per weight of Basidiomycotina.

In such a combination, *Ganoderma Lucidum* and/or *Coriolus versicolor* may be selected as the Basidiomycotina component. Preferably, *Ganoderma Lucidum* and *Coriolus versicolor* are used. A preferred ratio for the total quantity of Basidiomycotina is between about 1 and 4 parts per weight of *Coriolus versicolor* to about 2 parts per weight of *Ganoderma Lucidum*. Preferably, a ratio of about 1 part per weight of *Coriolus versicolor* to about 2 parts per weight of *Ganoderma Lucidum* is be used. More specifically, about 5 parts per weight of *Coriolus versicolor*, about 1.5–6 parts per weight of the root of an Araliaceae plant (preferably *Panax japonicus*) and about 10 parts per weight of *Ganoderma Lucidum* are used. More preferably, about 5 parts per weight of *Coriolus versicolor*, about 3 parts per weight of the root of an Araliaceae plant (preferably *Panax japonicus*) and about 10 parts per weight of *Ganoderma Lucidum* are used.

In addition, about 10 parts per weight of *Coriolus versicolor*, about 1.5–6 parts per weight of the root of an Araliaceae plant (preferably *Panax japonicus*) and about 5 parts per weight of *Ganoderma Lucidum* may be used.

Another preferred ratio is about 0.5–2 parts per weight of the root of an Araliaceae plant and about 2 parts per weight of Basidiomycotina. More preferably, a ratio of about 0.75–1.25 parts per weight of the root of an Araliaceae plant to about 2 parts per weight of Basidiomycotina is used. Most preferably, about 1 part per weight of the root of an Araliaceae plant to about 2 parts per weight of Basidiomycotina is used.

More specifically, *Ganoderma Lucidum* and *Coriolus versicolor* are used as Basidiomycotina in a ratio of 1 part per weight of *Coriolus versicolor*, about 0.5–2 parts per weight of the root of an Araliaceae plant and about 1 part per weight of *Ganoderma Lucidum*. More preferably, about 0.75–1.25 parts per weight of the root of an Araliaceae plant can be used, and most preferably 1 part per weight can be used.

In another embodiment, about 5–10 parts per weight of *Coriolus versicolor*, about 3–10 parts per weight of the root of an Araliaceae plant and about 10 parts per weight *Ganoderma Lucidum* are used. Preferably, the root of *Panax japonicus* is selected as the root of the Araliaceae plant.

For any of the above-mentioned combination, either *Ganoderma Lucidum* and *Coriolus versicolor* (i.e., the fruiting bodies of either) may be used alone as Basidiomycotina. Preferably, *Panax ginseng* or *Panax japonicus* is used as the Araliaceae plant component. More preferably, *Panax japonicus* can be used, but therapeutically effective compositions also can be obtained even if *Panax ginseng* is substituted for *Panax japonicus*.

A representative method will now be described for making a composition having a 1:1:1 weight ratio of the fruiting bodies of *Ganoderma Lucidum*, the fruiting bodies of *Coriolus versicolor* and *Panax japonicus* (root). For example, 6 g of the fruiting bodies of *Ganoderma Lucidum*, 6 g of the fruiting bodies of *Coriolus versicolor* and 6 g of *Panax japonicus* can be combined, mixed and crushed into splinters of approximately 5 mm in size 500 ml of distilled water can be added to this crushed product and the mixture can be boiled for 3 hours using a reflux condenser. After which, the solution is filtered to yield a stock solution composition.

This stock solution may be diluted if necessary for certain uses. If dilution is necessary, various dilution ratios may be utilized, such as dilution ratios ranging between 2 and 300 fold, preferably between 2 and 20 fold and most preferably between 4 and 16 fold. While no particular restrictions are placed on the dilution technique, similar to the extraction process, it is recommended to use water.

Moreover, the solvent can be removed from the stock solution using various appropriate concentrating methods to prepare solid extracts.

For compositions prepared in such a manner, whether in a solution or suspension state, preferably the compositions have an oxidation-reduction potential of about +1230 mV or less. More preferably, the compositions have an oxidation-reduction potential of about +900 mV or lower. Such compositions have exhibited potent anti-tumor activity.

The oxidation-reduction potential value is measured in an aqueous solvent, and preferably in water. The oxidation-reduction potential can be measured directly in the above-described stock solution or in a water-diluted solution. If the composition has been solidified, the solid should be dissolved or suspended using an adequate solvent, such as water, before measuring the oxidation-reduction potential.

As used herein, the oxidation-reduction potential of a solution of a particular composition is determined as follows. The oxidation-reduction potential is the potential of an oxidation-reduction electrode observed when the electrode is dipped into a test solution. In case of using reference electrode, a single potential of the reference electrode, which is the potential difference between an oxidation-reduction electrode (e.g. platinum electrode) and reference electrode is first determined. Thereafter, the reference electrode of the electrode potential measuring device is placed in the test solution and the potential difference is noted. The potential difference noted for the test solution plus the single potential is the oxidation-reduction potential for the solution. For example, if a platinum test electrode and a reference electrode (for example, AgCl (internal solution 3.3 mol/l KCl)) are used, the potential obtained by adding the single-electrode potential of the reference electrode with the potential difference between the reference electrode and the test solution is the oxidation-reduction potential. Throughout this specification, the oxidation-reduction potential was measured at a test solution temperature of 25° C.

After the composition is prepared or after it is dissolved or suspended, its oxidation-reduction potential typically changes over time. The oxidation-reduction potential should therefore be checked from time to time. Preferably, the solution is used when the oxidation-reduction potential is about +900 mV or less. The oxidation-reduction potential of the composition should also be checked before each administration. Preferably, the composition and solutions thereof are stored at 25° C. and the temperature in the measurement room should also be 25° C.

The oxidation-reduction potential of the resulting composition appears to be significant because, especially for compositions having an oxidation-reduction potential of +900 mV or less, a negative correlation exists between the oxidation-reduction potential of the composition and its anti-tumor activity. In other words, the lower the oxidation-reduction potential, the stronger the anti-tumor activity.

As a result, the anti-tumor activity and hypoglycemic effect of the subject composition can be estimated before administering the composition by measuring its oxidation-reduction potential before the composition is administered. In this manner, treatment efficacy can be increased.

In more particularly preferred compositions of the present teaching, the oxidation-reduction preferably is +330 mV or lower, more preferably is +300 mV or lower and most preferably is +250 mV or lower. Further, the oxidation-reduction preferably is –1200 mV or higher and more preferably is –300 mV or higher.

The present compositions may comprise only Basidiomycotina extracted components and Araliaceae plant root extracted components. However, other active or inactive ingredients can also be included as long as the additional ingredients do not inhibit the synergistic effect of the above-mentioned 2 extracted components. For example, the extracted components described herein can be mixed with pharmaceutically acceptable carriers and additives in order to prepare compositions suitable for administration. While no special restrictions are placed on form, the compositions can be manufactured in the form of a solution, syrup, suspension, emulsion, granules, tablets, pills, capsules, cream, lozenge, chewable tablets, suppository, eye drops, injection, aerosol, elixir and the like. The present compositions also can be used in a solid (powder) form and solutions can be reconstituted by adding water at the time of administration. Thus, various administration routes are available for the present compositions.

The present compositions have been shown to have anti-tumor activity, especially with respect to leukemia, cervical carcinoma, lung carcinoma, cancer of the ovaries, breast cancer (including metastatic cancer) and cutaneous carcinoma (including metastatic cancer). An example of leukemia is erythroblastic leukosis. Thus, the present compositions can be used as anti-tumor agents for mammals, including for example humans, primates, cattle, horses, dogs and cats.

While the extracted components of Basidiomycotina are known to have anti-tumor activity and the extracted components of the root of Araliaceae plants are known to have an anti-tumor activity, the present compositions have demonstrated an unexpectedly potent anti-tumor activity, as compared to the anti-rumor activities of the individual components.

In addition, the present compositions also have a hypoglycemic effect and the present compositions have been shown to be effective in both insulin dependent diabetes mellitus and non-insulin dependent diabetes mellitus.

Moreover, the present compositions have not demonstrated any adverse effects. In fact, the present compositions may be useful to reduce and alleviate the adverse effects of other drugs.

For example, when the present compositions have been administered to human patients as anti-tumor agents, the compositions have demonstrated various beneficial effects, such as alleviating pain, improving appetite and enabling the patient to sleep well, in addition to causing tumors to heal or regress. When administered to humans to reduce blood sugar levels, the present composition again demonstrated various beneficial effects, such as alleviating pain in the body, especially significantly relieving headaches and numbness of the limbs, increasing appetite, recovering eyesight, reducing stress and enabling the patient to sleep well, in addition to causing blood glucose levels to decrease.

While the present compositions can be administered in therapeutically effective amounts either orally or parenterally, preferably the compositions are administered orally. General doses appropriate for oral administration are indicated below. Naturally, the dose should be appropriately adjusted according to the patient's symptoms and stamina. Generally speaking, usual or normal dosages are, for example, a daily dosage of the extracted components obtained from between 200 mg and 2 g Basidiomycotina and between 100 mg and 1 g root of an Araliaceae plant, per 1 kg of body weight. These doses are preferably administered between 1 and 3 times per day.

Especially when used as an anti-tumor agent, preferably the extracted components are administered that have been extracted from raw materials in a ratio of about 0.27 g Basidiomycotina and the root of an Araliaceae plant per 1 kg of body weight per day. More preferably, the extracted components are administered that have been obtained from raw materials in a ratio of about 0.18 g Basidiomycotina/1 kg of body weight/day and the extracted components obtained from about 0.09 g, root of an Araliaceae plant/1 kg body weight/day.

When used as a hypoglycemic agent, preferably the extracted components are administered that have been extracted from raw materials in a ratio of about 0.12 g Basidiomycotina and the root of an Araliaceae plant/1 kg of body weight/day. More preferably, the extracted components are administered that have been obtained from raw materials in a ratio of about 0.08 g Basidiomycotina/1 kg body weight/day and the extracted components obtained from about 0.04 g root of an Araliaceae plant/1 kg body weight/day.

When used as a hypoglycemic agent (i.e. to reduce blood sugar levels), the composition is preferably administered together with water and/or alcohol extracts of the root of an Araliaceae plant. Such alcohol extracts can be obtained by using the root of an Araliaceae plant, preferably medicinal ginseng and most preferably *Panax japonicus*, in the form of splinters or powder (preferably splinter approximately 5 mm in size). Between about 300 and 600 parts per weight of a 40% ethyl alcohol solution is added to between 10 and 20 parts per weight of the splinters. Heat-extraction is performed by beating the solution to between 80 and 100° C. until the alcohol evaporates almost completely.

Because the toxicity of the present compositions appears to be very low and does not appear to cause serious adverse effects, a high dose can also be safely administered if needed, based upon the symptoms.

The recommended dosage form for oral administration is solution or syrup. Water is recommended as the administration medium.

In summary, the following representative aspects of the present teachings are provided herein:

(1) Compositions comprising a therapeutically effective amount of active ingredients found in one or more types of Basidiomycotina that belong to polyporaceae Basidiomycotina and the root of a plant that belongs to Araliaceae. These active ingredients may be prepared synthetically or by isolation from natural products. In a preferred aspect of the present teachings, a ratio of between about 0.5 and 2 parts per weight of the root of an Araliaceae plant to 2 parts per weight Basidiomycotina is utilized and the active ingredients are isolated therefrom. Such compositions have shown hypoglycemic (blood sugar reducing) effects.

(2) The above-mentioned compositions of paragraph (1), wherein the above-mentioned one or more types of Basidiomycotina are *Ganoderma Lucidum* and/or *Coriolus versicolor*.

(3) The above-mentioned compositions according to paragraphs (1) and (2), wherein the above-mentioned plant that belongs to Araliaceae is medicinal ginseng.

(4) The above-mentioned compositions according to paragraphs (1) through (3), wherein the above-mentioned Araliaceae plant is *Panax ginseng* and/or *Panax japonicus*.

(5) The above-mentioned compositions according to paragraphs (1) through (4), wherein the oxidation-reduction potential is +1230 mV or less.

(6) Compositions comprising a therapeutically effective amount of hot-water extracted components of one or more types of Basidiomycotina that belong to polyporaceae Basidiomycotina and the hot water extracted components of the root of a plant that belongs to Araliaceae. Additional compositions include such extracted components in a solution containing 40% or more alcohol and the root of a plant that belongs to Araliaceae.

(7) The above-mentioned compositions according to paragraph (6) which have a hypoglycemic effect.

(8) Compositions comprising extracted components of one or more types of Basidiomycotina that belong to polyporaceae Basidiomycotina and extracted components of the root of a plant that belongs to Araliaceae.

(9) Method for treating patients by administering a therapeutically effective amount of a composition according to any of paragraphs (1) through (8). For example, such compositions may be administered to patients whose blood glucose level should be reduced.

(10) Compositions comprising active ingredients of one or more types of Basidiomycotina that belong to polyporaceae Basidiomycotina and the root of a plant that belongs to Araliaceae. These active ingredients may be prepared synthetically or by isolation from natural products. Preferably, a ratio of between 0.5 and 2 parts per weight of the root of an Araliaceae plant to 2 parts per weight Basidiomycotina is utilized and the active ingredients are isolated therefrom. Such compositions have shown anti-tumor activity.

(11) The above-mentioned compositions according to paragraph (10), wherein the above-mentioned one or more types of Basidiomycotina is *Ganoderma Lucidum* and/or *Coriolus versicolor*.

(12) The above-mentioned compositions according to paragraphs (10) and (11), wherein the above-mentioned plant that belongs to Araliaceae is medicinal ginseng.

(13) The above-mentioned compositions according to paragraphs (10) through (12), wherein the above-mentioned plant that belongs to Araliaceae is *Panax ginseng* and/or *Panax japonicus*.

(14) The above-mentioned compositions according to paragraphs (5) through (8) and (10) through (13), wherein the oxidation-reduction potential is +1230 mV or less.

(15) Methods for treating patients by administering a therapeutically effective amount of a composition according to any of paragraphs (10) through (14). Such compositions may, for example, be administered to patients having tumors and preferably to patients that have been diagnosed with terminal cancer.

(16) Compositions comprising components extracted from about 10 parts per weight *Coriolus versicolor* and between about 1.5 and 6 parts per weight *Panax japonicus* to about 5 parts per weight *Ganoderma Lucidum*.

(17) The above-mentioned compositions according to paragraph (16), wherein the oxidation-reduction potential is +1230 mV or less.

(18) Methods for treating patients by administering a therapeutically effective amount of a composition according to any of paragraphs (16) and (17).

Other aspects of the present teachings are also provided throughout the specification.

Each of the additional examples, compositions and method steps disclosed above and below may be utilized separately or in conjunction with other examples to provide improved compositions and methods for making and using such compositions. Representative examples of the present invention, in which such examples, compositions and method steps are in conjunction or in farther detail, will now be described. This detailed description is merely intended to teach a person of skill in the art further details for practicing preferred aspects of the present teachings and is not intended to limit the scope of the invention. Only the claims define the scope of the claimed invention. Therefore, combinations of features and steps disclosed in the following detail description may not be necessary to practice the invention in the broadest sense, and are instead taught merely to particularly describe representative examples of the invention.

EXAMPLE 1

Preparation of a First Representative Composition

The fruiting bodies of *Ganoderma Lucidum*, the fruiting bodies of *Coriolus versicolor* and the root of *Panax japonicus* C. A. Meyer were used. The black fruiting bodies of *Ganoderma Lucidum* were used and were naturally ripened and collected during summer in a forest in north China. The black fruiting bodies were then air-dried at room temperature in the dark. Native fruiting bodies of *Coriolus versicolor* were collected during summer in Japan and then air-dried at room temperature in the dark. The roots of full-grown plants of *Panax japonicus* were collected during summer in Japan and then air-dried at room temperature in the dark.

6 g *Ganoderma Lucidum*, 6 g *Coriolus versicolor* and 6 g *Panax japonicus* were weighed separately and the mixture of these three raw materials was crushed into splinters of about 5 mm in size. 500 ml of water (ion-exchanged water, purity: 1 ES/cm or lower) was added to this mixture and it was boiled for 2 hours under reflux using a reflux condenser. The solution was then filtered and an extracted composition was obtained. It was determined that 1 ml of this composition comprised extracted components equivalent to approximately 0.012 g of *Ganoderma Lucidum*, approximately 0.012 g of *Coriolus versicolor* and approximately 0.012 g of *Panax japonicus*. The solution was further diluted, using the above-mentioned ion-exchanged water, at ratios of 1/4, 1/8, 1/16, 1/32, 1/64, 1/128 and 1/256.

EXAMPLE 2

Preparation of a Second Representative Composition 6 g *Ganoderma Lucidum*, 6 g *Coriolus versicolor* and 6 g *Panax japonicus* were weighed separately and a mixture of these three raw materials was ground into a powder. The powered mixture was then processed in the same manner as in Example 1 in order to prepare the composition of Example 2. The composition of Example 2 was diluted in the same manner as in Example 1.

EXAMPLE 3

Verification of Anti-Tumor Activity and Proliferation Inhibition in Human Leukocyte Cancer Cells (K562 Cells)

150 $\mu$l (20×10$^3$ cells) of a culture solution of the K562 cell system was deposited into each of the respective wells of a microtiter plate. The K562 cell system was provided by the Department of Clinical Microbiology Rigshopitalet, Aafs, 7806 at The National University Hospital of Denmark 50 $\mu$l of the stock solutions, as well as each of the dilution solutions, prepared according to the above-mentioned Examples 1 through 2 were added to the respective wells and the cells were cultured at 37° C. Cell proliferation after 24 hours, 48 hours, 72 hours and 96 hours of culturing was assessed using the SRB (sulfohodamine B) method.

The SRB method was implemented as follows. 50 $\mu$l of 80% TCA (trichloroacetic acid) was added to each well and the cells were immobilized for 1 hour. Next, the cells were rinsed 4 times and thoroughly dried. 200 $\mu$l of 4% SRB (sulfohodamine B) was added to each well, the cells were stained for 30 minutes, rinsed 4 times and then dried. 10 mM of unbuffered Tris base was added to each well and stirred for 5 minutes. After which, the light absorption of the solution in each well was measured at a wavelength of 490 nm. The ratio of the cell count after culturing for a set time, obtained from these results, and the initial cell count, was used as the proliferation inhibition ratio (%).

The results related to the composition obtained in each of Examples 1 and 2 are shown in Tables 1 and 2. As shown in Tables 1 and 2, the stock solution and the dilution solutions (up to about the 16-fold dilution solution) of the composition obtained in Example 1 showed remarkable proliferation inhibition in the K562 cell system. The stock solution and the dilution solutions (up to about the 8-fold dilution solution) of the composition obtained in Example 2 also showed remarkable proliferation inhibition in the K562 cell system. These results indicate that these compositions have anti-tumor activity and also indicate that extraction from splinters yields more potent anti-tumor activity.

TABLE 1

K562 cell proliferation inhibition ratio (%)

| Dilutions | 24 hrs | 48 hrs | 72 hrs | 96 hrs |
|---|---|---|---|---|
| 1:4 | 97.0 | 98.0 | 98.0 | 98.0 |
| 1:8 | 95.0 | 97.0 | 98.0 | 98.0 |
| 1:16 | 94.0 | 97.0 | 97.0 | 97.0 |
| 1:32 | 44.0 | 96.0 | 64.0 | 71.0 |
| 1:64 | 37.0 | 48.0 | 45.0 | 37.0 |
| 1:128 | 11.0 | 39.0 | 25.0 | 28.0 |
| 1:256 | 15.0 | 30.0 | 22.0 | 23.0 |

TABLE 2

K562 cell proliferation inhibition ratio (%)

| Dilutions | 24 hrs | 48 hrs | 72 hrs | 96 hrs |
|---|---|---|---|---|
| 1:4 | 92.4 | 95.3 | 96.9 | 97.9 |
| 1:8 | 86.7 | 89.0 | 92.9 | 96.0 |
| 1:16 | 33.7 | 25.4 | 16.8 | 17.4 |
| 1:32 | 23.6 | −17.2 | −28.1 | −3.8 |
| 1:64 | −22.8 | 10.1 | −30.1 | −3.4 |
| 1:128 | −9.6 | −32.4 | −17.13 | −9.6 |
| 1:256 | −0.61 | −13.5 | −37.74 | 3.20 |

EXAMPLE 4

Measurement of the Oxidation-reduction Potential of the Compositions

Each of the diluted compositions obtained in Example 1 were incubated at 25° C. for 24 hours and the oxidation-reduction potential (mV) of each solution was measured. An oxidation-reduction measuring device (HM-14P, manufactured by Touaku Denpa Kogyou, platinum electrode, reference electrode (silver chloride, internal solution 3.3 mol/l KCl) was used to measure the oxidation-reduction potential and the temperature in the measurement room was 25° C. At 25° C., the single-electrode potential of the reference electrode was 206 mV. The potential readings are shown in Table 3. The oxidation-reduction potentials were obtained by adding 206 mV to each of the potentials shown in Table 3.

TABLE 3

Oxidation-reduction potential [mV]

| Dilutions | 24 hrs |
|---|---|
| 1:4 | 10.0 |
| 1:8 | 22.0 |

TABLE 3-continued

Oxidation-reduction potential [mV]

| Dilutions | 24 hrs |
|---|---|
| 1:16 | 43.7 |
| 1:32 | 179.7 |
| 1:64 | 175.7 |
| 1:128 | 195.0 |
| 1:256 | 176.7 |

Thus, the oxidation-reduction potential, for example, of the 1:4 dilution was 226 mV as used throughout this specification. Further, the correlation between the oxidation-reduction potential of the composition at different dilution rates and the cell proliferation inhibition rate (after 24 hours), measured in Example 3, was calculated and found to be −0.960. It appears, therefore, that there is strong negative correlation between the oxidation-reduction potential and the cell proliferation inhibition.

EXAMPLE 5

Clinical Administration to Cancer Patients

A stock solution of a composition was obtained using the same process as in Example 1. This stock solution was continuously administered to 26 patients with severe cancer at doses of 150 ml each, 3 times a day for 35 days. The results showed that all the patients who were administered the composition either reported or were found to show alleviation of body pain, an increased appetite, an improvement in skin condition, reduced stress, better sleep and improvement of various body function disorders. Alleviation of complications and recovery were also observed.

Table 4 shows cases in which lesions regressed and cases in which lesions completely healed. Table 5 shows the results of blood tests on some of these patients and Table 6 shows the results of immunological tests on some of these patients.

TABLE 4

X-ray and sonography results

Item

B.O. (F, 28 years old, Stage = 3): complete healing of cervical carcinoma (15th day) and septicemia (29th day)
G.V. (M, 74 years old, Stage = 3): shrinking of carcinoma of the right lung from 7 × 5 cm to 3.5 × 4 cm (10th day)
P.V. (F, 52 years old, Stage = 4): 50% regression of cancer of the ovaries and metastatic breast cancer (21st day)
P.V. (F, 54 years old, Stage = 4): 50% regression of cancer with metastasis to the skin (35th day)
V.O. (F, 46 years old, Stage = 4): disappearance of ascites of right breast cancer, 50% regression of cutaneous carcinoma (35th day)

TABLE 5

| Test Item Test conditions | HGB (g/l) | | WBC ($10^{-9}$/l) | | RBC ($10^{-2}$/l) | | PLT ($10^{-9}$/l) | |
|---|---|---|---|---|---|---|---|---|
| | Before administration | 7$^{th}$ day | Before administration | 7$^{th}$ day | Before administration | 7$^{th}$ day | Before administration | 7$^{th}$ day |
| 1.S.T (Stage 4), M | 92 | 97 | 2.8 | 2.5 | 2.56 | 2.67 | 51 | 124 |
| 2.N.V (Stage 4), M | 117 | 116 | 7.79 | 8.86 | 4.29 | 4.22 | 247 | 259 |
| 3.G.I (Stage 3), F | 128 | 132 | 3.6 | 3.7 | 3.8 | 3.89 | 202 | 224 |
| 4.S.V (Stage 3), F | 117 | 136 | 3.51 | 4.2 | 3.78 | 4.11 | 189 | 215 |

HGB: Hemoglobin
RBC: Red blood cells
WBC: White blood cells
PLT: Platelets

TABLE 6

| Test Item Test conditions | CD4 | | CD8 | | NK + actLYM | |
|---|---|---|---|---|---|---|
| | Before administration | 14 days after | Before administration | 14 days after | Before administration | 14 days after |
| 1.S.T (Stage 4), M | 23.6% | 28.60% | 39.30% | 51.90% | 44.70% | 28.80% |
| 2.N.V (Stage 4), M | 51.10% | 47.30% | 20.50% | 28.60% | 33.60% | 38.50% |
| 3.G.I (Stage 3), F | 25.80% | 37.49% | 22.90% | 26.70% | 40.10% | 40.50% |
| 4.S.V (Stage 3), F | 40.40% | 40.20% | 27.60% | 30.20% | 20% | 24% |

CD4: Helper T cell
NK: Natural Killer cell
CD8: Killer T cell
actLYM: activated lymphocyte As shown in Tables 4–6, anti-tumor effects in humans produced by administration of the present compositions was confirmed. In other words, favorable therapeutic results were obtained for cervical carcinoma, lung carcinoma, cancer of the ovaries, breast cancer (metastasis), cutaneous carcinoma (metastasis), breast cancer and cutaneous carcinoma.

EXAMPLE 6

Clinical Administration to Diabetic Patients

A stock solution was obtained using the same process as in Example 1. In addition, *Panax japonicus* was crushed into splinters of about 5 mm in size. 500 parts per weight of a 40% ethyl alcohol solution was added to between 10 and 20 parts per weight of these splinters and heat-extraction was performed by heating the solution to between 80 and 100° C. until the alcohol evaporated almost completely, yielding a *Panax japonicus* extraction solution.

The stock solution of the composition of Example 1 and the *Panax japonicus* extraction solution were mixed at a ratio of 2:1. This solution was administered daily to 25 patients (11 males and 14 females) with diabetes mellitus at doses of 150 ml each, 2 times a day for 25 days.

The results showed that all the patients who were administered the composition either reported or were found to show alleviation of body pain, with especially significant improvement in headaches and numbness of the limbs, increased appetite, eyesight recovery, reduced stress and better sleep. Alleviation of complications and recovery were also observed. In some patients there was even recovery of sensation in their necrotic lower limbs.

The clinical results are shown in Table 7. As shown in Table 0.7, a decrease in the blood glucose level in all the patients following such clinical administration was confirmed. Administration of this composition was not associated with any adverse effects. In addition to improvement in the subjective symptoms, it also produced remarkable hypoglycemic effects.

TABLE 7

| Patient No. | Age | Sex | Kind * | Years of Disease | Blood glucose(mg/dl) | | [B]/[A](%) |
|---|---|---|---|---|---|---|---|
| | | | | | Before therapy[A] | After therapy[B] | |
| 1 | 15 | f | 1 | 6 | 279.0 | 142.2 | 50.9 |
| 2 | 22 | f | 1 | 3 | 378.0 | 104.4 | 27.6 |
| 3 | 31 | f | 1 | 17 | 162.0 | 124.2 | 76.7 |
| 4 | 37 | f | 1 | 23 | 183.6 | 115.2 | 62.7 |
| 5 | 40 | f | 1 | 30 | 165.6 | 149.4 | 90.2 |
| 6 | 56 | f | 1 | 14 | 196.2 | 97.2 | 49.5 |
| 7 | 57 | f | 1 | 30 | 246.6 | 106.2 | 43.1 |

TABLE 7-continued

| Patient No. | Age | Sex | Kind * | Years of Disease | Blood glucose(mg/dl) Before therapy[A] | Blood glucose(mg/dl) After therapy[B] | [B]/[A](%) |
|---|---|---|---|---|---|---|---|
| 8 | 16 | m | 1 | 10 | 243.0 | 133.2 | 54.8 |
| 9 | 16 | m | 1 | 9 | 252.0 | 151.2 | 60.0 |
| 10 | 18 | m | 1 | 10 | 210.6 | 109.8 | 52.1 |
| 11 | 22 | m | 1 | 11 | 237.6 | 104.4 | 43.9 |
| 12 | 35 | m | 1 | 1 | 153.0 | 104.4 | 68.2 |
| 13 | 21 | f | 2 | — | 296.0 | 136.8 | 46.2 |
| 14 | 50 | f | 2 | — | 149.0 | 122.4 | 82.1 |
| 15 | 54 | f | 2 | 20 | 246.6 | 106.2 | 43.1 |
| 16 | 55 | f | 2 | 9 | 326.0 | 162.0 | 49.7 |
| 17 | 69 | f | 2 | 10 | 234.0 | 91.8 | 39.2 |
| 18 | 74 | f | 2 | 16 | 165.6 | 120.6 | 72.8 |
| 19 | 49 | m | 2 | 8 | 198.0 | 117.0 | 59.1 |
| 20 | 49 | m | 2 | 16 | 196.2 | 117.0 | 59.6 |
| 21 | 51 | m | 2 | 14 | 158.4 | 81.0 | 51.1 |
| 22 | 56 | m | 2 | 1 | 180.0 | 95.4 | 53.0 |
| 23 | 56 | m | 2 | — | 492.0 | 118.8 | 24.1 |
| 24 | 56 | m | 2 | 16 | 296.0 | 88.2 | 29.8 |
| 25 | 59 | m | 2 | 3 | 199.8 | 136.8 | 68.5 |

* 1: insulin dependent diabetes mellitus, 2: insulin independent diabetes mellitus Further, it is noted that patients 13, 16, 20 and 22 were treated only with the present composition noted above (i.e. the solution of the composition of Example 1 and the *Panax japonicus* extraction solution mixed at a ratio of 2:1). Thus, 4 patients with NIDDM were treated with only the administration of the present composition. 13 patients with IDDM and 9 patients with NIDDM were treated with administration of both the present composition and insulin. All the patients had been treated previously with insulin before this test was conducted. Further, patients who were treated with both the present composition and insulin were given the same insulin doses as administered before the test was conducted.

Table 8 shows the mean blood glucose level of each group of patients. The results have been grouped according to the type of diabetes mellitus and the type of treatment. Before and after administration blood glucose levels, as well as the percentage of the blood glucose after the administration to the blood glucose level compared to before administration, are provided in Table 8.

TABLE 8

| Treatment | | Only the composition | | The composition and insulin | |
|---|---|---|---|---|---|
| | Case | IDDM | NIDDM | IDDM | NIDDM |
| Blood glucose (mg/dl) | Before | — | 249.6 | 225.6 | 237.7 |
| | After | — | 127.8 | 120.2 | 109.2 |
| After/Before (%) | | — | 51.20 | 53.30 | 45.90 |

As shown in Table 8, a remarkable decrease in the blood glucose level in all the patients following such clinical administration was confirmed. Administration of this composition was not associated with any adverse effects.

EXAMPLE 7

Clinical Administration to Cancer Patients

A stock solution of the composition was obtained using the same process as in Example 1. This stock solution was continuously administered orally to 3 patients with severe cancer at doses of 150 ml each, 3 times a day for 35 days. Only tie stock solution was administered to Patient 1 (P.V.) and no other medications were give. Patient 2 (Y.T.) was administered doses of 800 mg 5-FU, 6 times a day for 35 days as chemotherapy, in addition to administration of the stock solution. Patient 3 (N.V.) was irradiated using radioactive rays of 60 Gy, 4 times a day for 35 days as radiotherapy, in addition to administration of the stock solution. Blood tests and immunological tests were performed for each patient before and after the administrations.

As a control, Patient 4 (A.R.) was not administered any specific treatment during this time period. However, blood tests and immunological tests were also performed for Patient 4.

Table 9 shows the condition and the method of treatments for each patient. Table 10 shows the recovery or the improvement in condition reported by these patients. Tables 11 and 12 show the results of blood tests and the results of immunological tests on each patient, respectively.

TABLE 9

| Patient | Lesion | Stage | Administration of the composition | Other treatments |
|---|---|---|---|---|
| S.V. (F, 51 years old) | Breast cancer | 4 | 150 ml × 3 times/day × 35 days | None |
| Y.T. (M, 55 years old) | Lung cancer | 4 | 150 ml × 3 times/day × 35 days | Chemotherapy (5-FU 800 mg × 6 times/day) |
| N.V. (M, 65 years old) | Sarcoma | 4 | 150 ml × 3 times/day × 35 days | Radiotherapy (60 Gy × 4 times/day) |
| A.R. (F, 70 years old) | Large intestine cancer | 4 | None | None |

TABLE 10

| Patient | Treatment | Changes of subjective symptom |
|---|---|---|
| S.V. | Administration of the composition of Example 1 | alleviation of body pain improved appetite elimination of nausea pleasant sleep improvement of various body function disorders increased body strength improved skin condition improved bowel movements |
| Y.T. | Administration of the composition of Example 1 and chemotherapy | alleviation of body pain improved appetite reduced nausea better sleep improvement of various body function disorders increased body strength |
| N.V. | Administration of the composition of Example 1 and radiotherapy | alleviation of body pain improved appetite better sleep improvement of various body function disorders increased body strength |

TABLE 11

| | Before the administration | | | | After the administration | | | |
|---|---|---|---|---|---|---|---|---|
| Patient | HGB (g/l) | WBC ($10^{-9}$/l) | RBC ($10^{-2}$/l) | PLT ($10^{-9}$/l) | HGB (g/l) | WBC ($10^{-9}$/l) | RBC ($10^{-2}$/l) | PLT ($10^{-9}$/l) |
| S.V. | 86 | 2.4 | 2.43 | 156 | 97 (112.8)* | 2.5 (104.2) | 2.67 (109.9) | 124 (79.5) |
| Y.T. | 128 | 3.6 | 3.99 | 252 | 136 (106.25) | 4.2 (116.7) | 4.11 (103.0) | 215 (85.3) |
| N.V. | 117 | 7.79 | 4.29 | 247 | 116 (99.1) | 7.4 (95.0) | 4.04 (94.2) | 270 (109.3) |
| A.R. | 126 | 9.1 | 4.07 | 155 | 110 (87.3) | 5.9 (64.8) | 2.49 (61.2) | 251 (161.9) |

*The numbers in parentheses show the percentages of each count after the administration compared to each count before administration.

TABLE 12

| | Before the administration | | | | After the administration | | | |
|---|---|---|---|---|---|---|---|---|
| Patient | CD4 (%) | CD8 (%) | NK + ACTLYP (%) | NK (%) | CD4 (%) | CD8 (%) | NK + ACTLYP (%) | NK (%) |
| S.V. | 40.4 | 27.6 | 20 | 8.5 | 40.2 | 30.2 | 24 | 8.3 |
| Y.T. | 27.6 | 39.3 | 44.7 | 11.2 | 28.6 | 51.9 | 28.8 | 8.4 |
| N.V. | 51.1 | 20.5 | 33.6 | 15.5 | 47.3 | 28.6 | 38.5 | 20.8 |
| A.R. | — | — | — | — | — | — | — | — |

As shown in Table 10, all the patients who were administered the composition of Example 1 reported alleviation of body pain, increased appetite, better sleep and improvement of various body function disorders. Alleviation of complications and recovery were also observed.

Moreover, as shown in Table 11, treatment of Patient 1 (S.V.), which utilized only the administration of the present composition, improved the concentration of each constituent part of the blood. Further, Patient 2 (Y.T.—chemotherapy) and Patient 3 (N.V.—radiotherapy) showed improvements in the respective blood tests. Administration of the present composition also improved the immunological conditions of Patients 2 and 3, who were subjected to either chemotherapy or radiotherapy, as shown in Table 12.

EXAMPLE 8

Additional Representative Methods for Making the Present Composition

Although the previous examples have utilized hot water extracted components from polyporaceae Basidiomycotina and hot water (and/or alcohol) extracted components of the root of a plant that belongs to Araliaceae, other compositions are contemplated. For example, components may be extracted from the natural products using other extraction techniques. In one example, the starting materials may be subjected to an extraction process, the extracted components may be filtered and the vacuum distilled. The resultant may be sterilized, dried and then screened to form a powder.

Dried extracted components then may be formulated as powders, granules, capsules, tablets, etc. For example, the extracted components may be mixed with a binder, granulated and dried to form granules. These granules may be utilized as is or may be pressed into tablet or filled into capsules. The optional binder may be added either before or after granulating the dried extracted components. In the alternative, the extracted components may be dried and encapsulated. Further, other pharmaceutically acceptable additives may be added, including but not limited to one or more preservatives in order to extend the shelf-life of the composition.

Moreover, the active ingredients may be dissolved in a pharmaceutically acceptable solvent, filtered and packaged in ampoules. These ampoules may be sterilized. Again, other pharmaceutically acceptable additives may be added to the solution, including but not limited to one or more preservatives in order to extend the shelf-life of the composition.

Further, the active ingredients may be isolated and only the active ingredients may be utilized as therapeutic agents. The active ingredients may be characterized and then produced synthetically. In this case, the synthetically produced active ingredients may be utilized in powders, granules, capsules, tablets, ampoules, etc. in order to provide other vehicles for administering the present compositions to patients. Again, other various pharmaceutically acceptable additives may be added as necessary.

What is claimed is:

1. A composition comprising a hot water extract of a Basidiomycotina and a hot water extract of a ginseng root;
wherein the composition has an oxidation-reduction potential of less than about 1230 mv;

and said Basidomycotina is selected from the group consisting of *Ganoderma Lucidum, Coriolus versicolor* and a mixture thereof.

2. A composition according to claim 1, wherein the ginseng root is *Panax japonicus*.

3. A composition according to claim 2, wherein said extract is extracted from 10 parts per weight the *Coriolus versicolor*, between about 1.5 and 6 parts per weight of the *Panax japonicus* and about 5 parts per weight of the *Ganoderma Lucidum*.

4. A composition according to claim 3, wherein the composition has an oxidation-reduction potential less than about 330 mv.

5. A composition according to claim 4, wherein the composition exhibits anti-tumor activity.

6. A composition according to claim 5, wherein the composition treats tumors.

7. A composition according to claim 1, wherein said extract is extracted from between about 0.5 and 2 parts per weight of the ginseng root and about 2 parts per weight of the Basidiomycotina.

8. A composition according to claim 7, wherein the composition has an oxidation-reduction potential less than about 330 mv.

9. A composition according to claim 8, wherein the composition exhibits anti-tumor activity.

10. A composition according to claim 9, wherein the composition treats tumors.

11. A composition according to claim 1, wherein said extract is extracted from about 1 part per weight of the ginseng root and about 2 parts per weight of the Basidomycotina.

12. A composition according to claim 11, wherein the composition has an oxidation-reduction potential less than about 330 mv.

13. A composition according to claim 12, wherein the composition exhibits anti-tumor activity.

14. A Composition according to claim 13, wherein the composition treats tumors.

15. A composition according to claim 1, wherein said extract is extracted from about 1 part per weight the *Coriolus versicolor*, about 1 part per weight of the ginseng root, and about 1 part per weight of the *Ganoderma Lucidum*.

16. A composition according to claim 15, wherein the composition has an oxidation-reduction potential less than about 330 mv.

17. A composition according to claim 16, wherein the composition exhibits anti-tumor activity.

18. A composition according to claim 17, wherein the composition treats tumors.

19. A composition according to claim 4, wherein the composition exhibits a hypoglycemic effect.

20. A composition according to claim 19, wherein the composition treats diabetes.

21. A composition according to claim 8, wherein the composition exhibits a hypoglycemic effect.

22. A composition according to claim 21, wherein the composition treats diabetes.

23. A composition according to claim 11, wherein the composition exhibits a hypoglycemic effect.

24. A composition according to claim 23, wherein the composition treats diabetes.

25. A composition according to claim 15, wherein the composition exhibits a hypoglycemic effect.

26. A composition according to claim 25, wherein the composition treats diabetes.

27. A method of making a composition comprising the step of admixing a hot water extract of a Basidiomycotina and a hot water extract of a ginseng root; wherein the composition has an oxidation-reduction potential of less than about 900 mv; and said Basidomycotina is selected from the group consisting of *Ganoderma Lucidum, Coriolus versicolor* and a mixture thereof.

28. A method according to claim 27, wherein the ginseng root is *Panax japonicus*.

29. A method according to claim 28, wherein said extraction step is performed on 10 parts per weight the *Coriolus versicolor*, between about 1.5 and 6 parts per weight of the *Panax japonicus* and about 5 parts per weight of the *Ganoderma Lucidum*.

30. A method according to claim 29, wherein the composition has an oxidation-reduction potential less than about 330 mv.

31. A method according to claim 30, further comprises administering to a patient a therapeutically effective amount of the composition to treat tumors.

32. A method according to claim 30, further comprises administering to a patient a therapeutically effective amount of the composition to treat diabetes.

33. A method according to claim 27, wherein said extraction step is performed on between about 0.5 and 2 parts per weight of the ginseng root and about 2 parts per weight of the Basidiomycotina.

34. A method according to claim 33, wherein the composition has an oxidation-reduction potential less than about 330 mv.

35. A method according to claim 34, further comprises administering to a patient a therapeutically effective amount of the composition to treat tumors.

36. A method according to claim 34, further comprises administering to a patient a therapeutically effective amount of the composition to treat diabetes.

37. A method according to claim 27, wherein said extraction step is performed on about 1 part per weight of the ginseng root and about 2 parts per weight of the Basidomycotina.

38. A method according to claim 37, wherein the composition has an oxidation-reduction potential less than about 330 mv.

39. A method according to claim 38, further comprises administering to a patient a therapeutically effective amount of the composition to treat tumors.

40. A method according to claim 38, further comprises administering to a patient a therapeutically effective amount of the composition to treat diabetes.

41. A method according to claim 27, wherein said extraction step is performed on about 1 part per weight the *Coriolus versicolor*, about 1 part per weight of the ginseng root, and about 1 part per weight of the *Ganoderma Lucidum*.

42. A method according to claim 41, wherein the composition has an oxidation-reduction potential less than about 330 mv.

43. A method according to claim 42, further comprises administering to a patient a therapeutically effective amount of the composition to treat tumors.

44. A method according to claim 42, further comprises administering to a patient a therapeutically effective amount of the composition to treat diabetes.

* * * * *